(12) United States Patent
Kato et al.

(10) Patent No.: US 7,099,534 B2
(45) Date of Patent: Aug. 29, 2006

(54) OPTICAL TRANSMISSION DEVICE WITH OPTICAL WAVEGUIDE COUPLED TO OPTICAL DEVICE

(75) Inventors: Masayuki Kato, Kawasaki (JP); Akio Sugama, Kawasaki (JP); Koji Tsukamoto, Kawasaki (JP); Yasuo Yamagishi, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 140 days.

(21) Appl. No.: 10/158,016

(22) Filed: May 31, 2002

(65) Prior Publication Data

US 2002/0197010 A1 Dec. 26, 2002

(30) Foreign Application Priority Data

Jun. 25, 2001 (JP) .............................. 2001-191428

(51) Int. Cl.
*G02B 6/32* (2006.01)
(52) U.S. Cl. ......................... 385/33; 385/129
(58) Field of Classification Search ................. 385/33, 385/88–93, 50, 129, 73, 74; 359/281
See application file for complete search history.

(56) References Cited

U.S. PATENT DOCUMENTS

| | | | | |
|---|---|---|---|---|
| 4,563,057 A | * | 1/1986 | Ludman et al. ............... 385/74 |
| 4,798,428 A | * | 1/1989 | Karim et al. .................. 385/74 |
| 5,093,879 A | | 3/1992 | Bregman et al. |
| 5,168,401 A | * | 12/1992 | Endriz ......................... 359/625 |
| 5,216,730 A | | 6/1993 | Demeritt et al. |
| 5,241,612 A | * | 8/1993 | Iwama .......................... 385/74 |
| 5,253,319 A | * | 10/1993 | Bhagavatula ................ 385/129 |
| 5,315,431 A | * | 5/1994 | Masuda et al. .............. 359/281 |
| 5,430,751 A | | 7/1995 | Weterings ..................... 372/49 |
| 5,513,289 A | * | 4/1996 | Hosokawa et al. ........... 385/33 |
| 5,612,171 A | | 3/1997 | Bhagavatula ................ 430/321 |
| 5,943,463 A | | 8/1999 | Unuma et al. ............... 385/119 |
| 6,014,244 A | * | 1/2000 | Chang ......................... 359/281 |
| 6,118,915 A | * | 9/2000 | Sato ............................. 385/39 |
| 6,167,174 A | * | 12/2000 | Zhang et al. .................. 385/33 |
| 6,312,163 B1 | * | 11/2001 | Ono et al. ..................... 385/70 |

FOREIGN PATENT DOCUMENTS

| | | |
|---|---|---|
| DE | 4412254 | 10/1995 |
| JP | 2-284490 | 11/1990 |
| JP | 5-40214 | 2/1993 |
| JP | 5-264874 | 10/1993 |
| JP | 6-13699 | 1/1994 |
| JP | 2000-304966 | 11/2000 |

* cited by examiner

*Primary Examiner*—Joseph Williams
*Assistant Examiner*—Dalei Dong
(74) *Attorney, Agent, or Firm*—Staas & Halsey LLP

(57) ABSTRACT

An optical waveguide and a first lens are formed on an underlying surface. The optical waveguide guides light along a first direction. The first lens is continuous with one end of the waveguide and converges light radiated from the end plane of the optical waveguide and diverging along directions parallel to the underlying surface. A second lens converges light transmitted through the first lens and diverging along directions perpendicular to the underlying surface. A support member supports the first and second lenses. It is possible to prevent a shift of positions of the optical waveguide and lens to be caused by a temperature change and to prevent a light coupling efficiency from being lowered.

15 Claims, 9 Drawing Sheets

OPTICAL TRANSMISSION DEVICE WITH OPTICAL WAVEGUIDE COUPLED TO OPTICAL DEVICE

CROSS REFERENCE TO RELATED APPLICATION

This application is based on Japanese Patent Application No. 2001-191428, filed on Jun. 25, 2001, the entire contents of which are incorporated herein by reference.

BACKGROUND OF THE INVENTION

A) Field of the Invention

The present invention relates to an optical transmission device, and more particularly to an optical transmission device for optically coupling an optical waveguide formed on a substrate to another optical device.

B) Description of the Related Art

Optical communication is increasing its speed and capacity because of a broadening transmission band and development of wavelength division multiplexing. In order to configure a hardware infrastructure of an optical fiber network in a trunk communications network, optical switches are required for switching optical signals toward destinations.

An example of an optical switch is shown in FIG. 9A. The optical switch includes a plurality of optical splitters 100, an optical switch module 101, a plurality of optical multiplexers 110, and a plurality of optical amplifiers 111. An optical fiber 120 is connected to each optical splitter 100. A wavelength division multiplexed optical signal is supplied from the optical fiber 120 to the optical splitter 100. The optical splitter 100 splits the wavelength division multiplexed optical signal into a plurality of optical signals. Split optical signals are input to the optical switch module 101 at the succeeding stage.

The optical switch module 101 has a three-stage structure. Each stage is constituted of a plurality of optical switch substrates. At the first stage, the optical switch substrate is provided for each optical splitter 100 to switch optical signals from optical waveguides of each optical splitter 100. The optical switch substrate at the second stage switches optical signals from a plurality of optical switch substrates at the first stage. The optical switch substrate at the third stage switches optical signals from a plurality of optical switch substrates at the second stage.

The optical multiplexer 110 is provided for each optical switch substrate at the third stage to multiplex the optical signal output from each optical switch substrate at the third stage. The multiplexed optical signal is amplified by the optical amplifier 111. An optical connector 115 is provided for connection between the optical splitter 100 and optical switch substrate at the first stage of the optical switch module 101, between the optical switch substrate at each stage of the optical switch module 101 and optical switch substrate at the succeeding stage, and between the optical switch substrate at the third stage and optical multiplexer 110.

FIG. 9B is a plan view of the optical switch substrate of the optical switch module 101 shown in FIG. 9A. An XY rectangular coordinate system is defined on the surface of a rectangular substrate 125, the X- and Y-axes being parallel to the sides of the rectangle. A plurality of input side optical waveguides 130 are disposed along one side parallel to the Y-axis to transmit light along the X-axis direction. A collimator lens 131 and a beam deflection element 132 are disposed on the surface of the substrate 125 in correspondence with each input side optical waveguide 130.

A beam deflection element 134 on the output side is disposed in correspondence with each beam deflection element 132, with a slab optical waveguide 133 being interposed therebetween. A condenser lens 135 and output side optical waveguide 136 are disposed in correspondence with each beam deflection element 134.

The input side beam deflection element 132 changes the propagation direction of a light beam in the substrate plane. The light beam with a changed propagation direction propagates through the slab optical waveguide 133 and becomes incident upon the output side beam deflection element 134. The beam deflection element 134 changes the propagation direction of the light beam to make it incident upon the corresponding condenser lens 135. The condenser lens 135 converges the light beam at the input end of the corresponding output side optical waveguide 136.

By deflecting a light beam to a desired direction by the input side beam deflection element 132, the optical signal input to the input side optical waveguide 130 can reach a desired output side optical waveguide 136. An optical signal can be switched by controlling the deflection direction at each time slot of the optical signal.

A method of connecting the output side optical waveguide 136 shown in FIG. 9B to the input side optical waveguide of, for example, the optical multiplexer 110 shown in FIG. 9A, is disclosed in JP-A-2000-304966 and JP-A-5-40214.

According to the invention disclosed in JP-A-2000-304966, a lens is disposed in correspondence with each output side optical waveguide between the output side and input side optical waveguides. Each lens converges light output and diverged from a corresponding output side optical waveguide at the input end of the corresponding input side optical waveguide. Since the output ends of the output side optical waveguides are disposed in line, the lenses are made of a micro lens array.

According to the invention disclosed in JP-A-5-40214, a collimator lens and a condenser lens are disposed in correspondence with each output side optical waveguide between the output side and input side optical waveguides. Light output and diverged from each output side optical waveguide is changed to a parallel light flux by a corresponding collimator lens, and this parallel light flux is converged at the input end of the input side optical waveguide by the condenser lens. These collimator lenses and condenser lenses are also made of micro lens arrays. Since the light beam between the collimator lens and condenser lens is a parallel light flux, a position alignment precision of a space between the collimator lenses and condenser lenses can be relaxed. Since the lenses have a sealing structure, the inside of the optical system can be protected. The influence of attached dusts can be mitigated.

JP-A-5-264874 discloses an optical system of converging light radiated from a light source and makes the light incident upon the input end of an optical fiber. By utilizing a thermal expansion of components for mounting optical elements, a change in the focal length of a lens to be caused by a temperature change can be compensated.

A position displacement between an optical waveguide and a lens to be caused by a temperature change is required to be suppressed in order to maintain high a coupling efficiency between the output side and input side optical waveguides. A position displacement (along a direction parallel to the propagation direction of a light beam) to be caused by a change in the focal length of a lens to be caused by a temperature change can be compensated by the method of utilizing the thermal expansion of mount components disclosed in JP-A-5-264874. If the optical waveguide is of a single mode, the position precision of 1 µm or smaller is necessary with respect to two directions perpendicular to the propagation direction of a light beam.

If lenses are made of a micro lens array, a distance between lenses changes because of thermal expansion of lens material. If the positions of a particular optical waveguide and a particular lens are set at a high precision, the positions of other optical waveguides and lenses are displaced.

SUMMARY OF THE INVENTION

An object of this invention is to provide an optical transmission device capable of preventing a position displacement between optical waveguides and lenses to be caused by a temperature change and preventing an optical coupling efficiency from being lowered.

According to one aspect of the present invention, there is provided an optical transmission device comprising: at least one optical waveguide end structure formed on an underlying surface, said optical waveguide end structure including an optical waveguide for guiding light along a first direction parallel to the underlying surface and a first lens formed on the underlying surface and being continuous with the optical waveguide at one end thereof, said first lens converging light that is radiated from the end of said optical waveguide and diverges along directions parallel to the underlying surface; a second lens for converging light that is transmitted through said first lens and diverges along directions perpendicular to the underlying surface; and a support member for supporting said first and second lenses.

According to another aspect of the invention, there is provided an optical transmission device comprising: first and second optical connectors each having an optical waveguide end structure, a second lens and a support member, the optical waveguide end structure being formed on an underlying surface and including an optical waveguide for guiding light along a first direction parallel to the underlying surface and a first lens being formed on the underlying surface and being continuous with the optical waveguide at one end thereof, the first lens converging light that is radiated from the end of the optical waveguide and diverges along directions parallel to the underlying surface, the second lens converging light that is transmitted through the first lens and diverges along directions perpendicular to the underlying surface, and the support member supporting the first and second lenses; and a coupling member for removably coupling said first and second optical connectors so that a light beam propagating in the optical waveguide of said first optical connector and converged by the first and second lenses is converged by the second and first lenses of said second optical connector toward one end of the optical waveguide of said second optical connector.

The first and second lenses can converge a light beam radiated and diverging from the optical waveguide. Since the optical waveguide and first lens are formed on the same substrate, both the optical waveguide and first lens can be easily aligned in position. A cylindrical surface lens can be used as the second lens. If the cylindrical surface lens is used, the position alignment along a direction parallel to the generating line of the curved surface is not required to be strict. It is therefore easy to align the positions of the second lens and optical waveguide. A shift in positions of the optical waveguide and lens to be caused by a temperature change can be avoided.

In this specification, the term "cylindrical surface lens" is intended to mean a lens having a cylindrical surface such as a circular cylindrical surface, a parabolic cylindrical surface, etc.

DESCRIPTION OF THE PREFERRED EMBODIMENTS

Figure 1A:
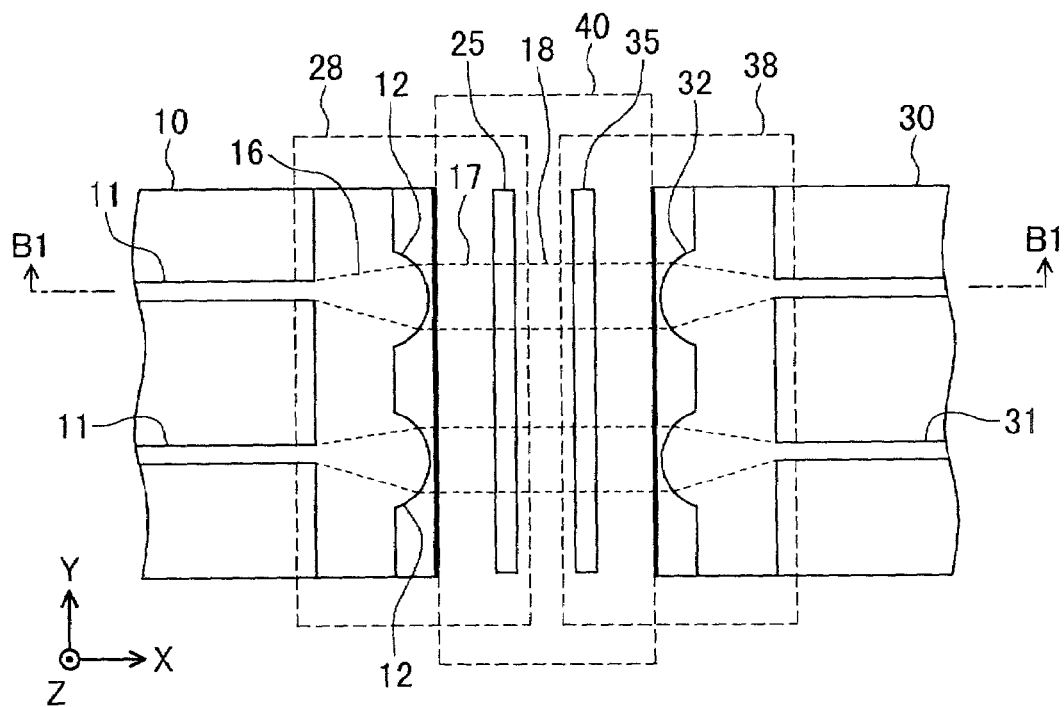
FIGS. 1A and 1B are a plan view and a cross sectional view of an optical transmission device according to a first embodiment of the invention.
Figure 1B:
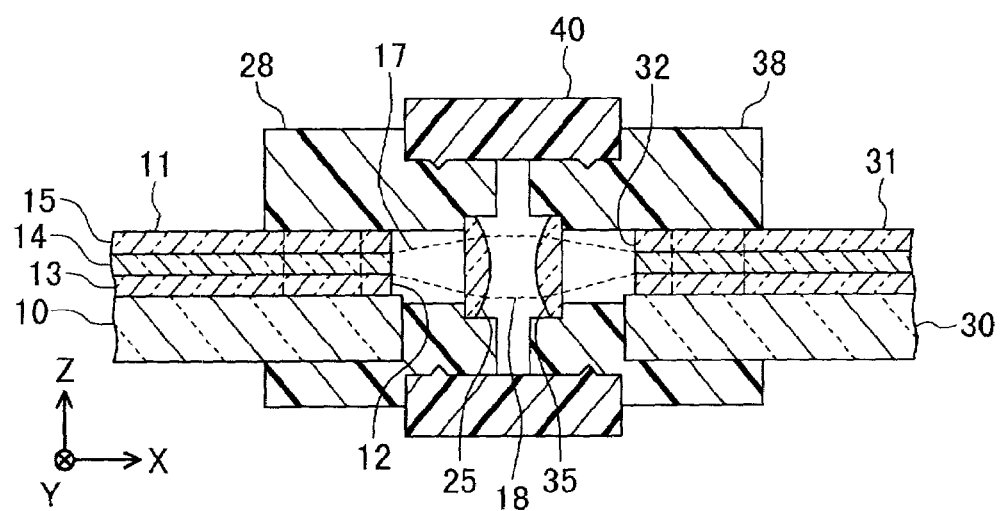
Figure 2:
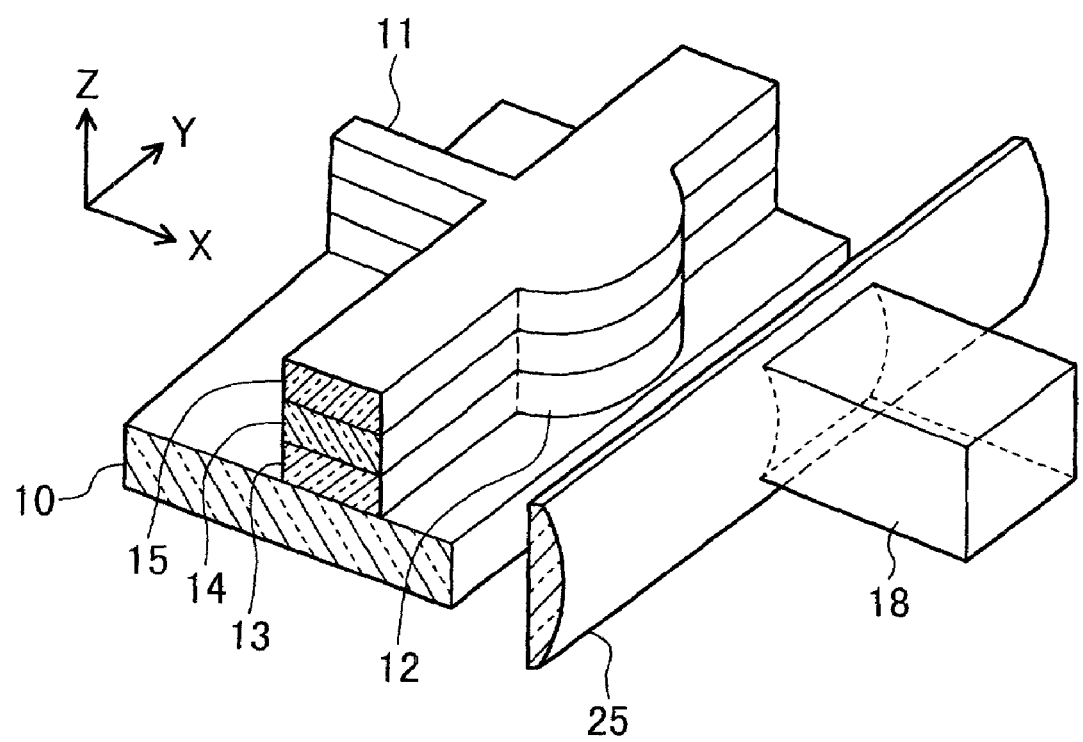
FIG. 2 is a perspective view showing the main part of the optical transmission device of the first embodiment.

With reference to FIGS. 1A and 1B and FIG. 2, the first embodiment of the invention will be described. FIG. 1A is a plan view of an optical transmission device of the first embodiment, and FIG. 1B is a cross sectional view taken along one-dot chain line B1—B1 shown in FIG. 1A. FIG. 2 is a perspective view partially broken of the main part of the optical transmission device of the first embodiment.

As shown in FIG. 1A, the optical transmission device of the first embodiment includes an optical waveguide substrate 10, an external cylindrical surface lens 25 and a connector 28 respectively on the transmission side, an optical waveguide substrate 30, an external cylindrical surface lens 35 and a connector 38 respectively on the reception side, and a sleeve 40. Consider an XYZ rectangular coordinate system having as the ZY plane the surfaces of the transmission side optical waveguide substrate 10 and reception side optical waveguide substrate 30, as the X-axis the propagation direction of an optical signal, and as the Z-axis the normal direction of the substrate.

The transmission side optical waveguide substrate 10 is made of silicon, glass or the like. A plurality of optical waveguides 11 are formed on the surface of the transmission side optical waveguide substrate 10. Although only two optical waveguides are shown in FIG. 1A, more optical waveguides are usually disposed. Each optical waveguide 11 propagates light along a direction parallel to the X-axis, and the output end of the optical waveguide 11 is disposed in parallel to the Y-axis. An internal cylindrical surface lens 12 is formed on the substrate surface continuously with the output end of each optical waveguide 11. All the internal cylindrical surface lenses 12 have the same shape so that by moving in translation one internal cylindrical surface lens 12 along a direction parallel to the Y-axis, it can be superposed upon another internal cylindrical surface lens 12.

As shown in FIG. 1B and FIG. 2, the optical waveguide 11 and internal cylindrical surface lens 12 each have a three-layer structure of a lower clad 13, a core 14 and an upper clad 15. The core 14 has a refractive index larger than those of the upper and lower clads 15 and 13. This three-layer structure is formed by sequentially coating photopolymer on the surface of the substrate 10 and patterning photopolymer layers by photolithography techniques. The width of the optical waveguide 11 and the thickness of the core 14 is about 5 to 10 μm.

Each internal cylindrical surface lens 12 has a curved surface having a straight line parallel to the Z-axis as its generating line. The internal cylindrical surface lens 12 converges in the XY plane a light beam 16 radiated and diverging from the output end of the optical waveguide 11. The curved surface of the internal cylindrical surface lens 12 is optically designed in such a manner that the light beam transmitted through the lens is changed to approximately a parallel light flux in the XY plane. Therefore, a light beam 17 transmitted through the internal cylindrical surface lens 12 is changed to approximately a parallel light flux in the XY plane.

The internal cylindrical surface lens 12 has a three-layer structure similar to the optical waveguide 11. A light beam is therefore confined in the core 13 between the output end of the optical waveguide 11 and output end of the internal cylindrical surface lens 12, and will not diverge in the ZX plane. The light beam 17 radiated from the output end of the internal cylindrical surface lens 12 diverges along the directions in the ZX plane as shown in FIG. 1B.

The light beam 17 transmitted through the internal cylindrical surface lens 12 becomes incident upon the external cylindrical surface lens 25. The relative position of the external cylindrical surface lens 25 to the optical waveguide substrate 10 is fixed by the connector 28. The external cylindrical surface lens 25 has a curved surface having a straight line parallel to the Y-axis as its generating line so that the light beam 17 is converted along the direction in the ZX plane. The curved surface of the external cylindrical surface lens 25 is optically designed in such as manner that the light beam transmitted through the lens is changed to approximately a parallel light flux along the direction in the ZX plane. A light beam 18 transmitted through the external cylindrical surface lens 25 is changed to a parallel light flux along the direction in both the XY and ZX planes.

The diameter of the light beam 18 is set preferably to about 300 to 400 μm. A diverging angle of a light beam radiated from the output end of the optical waveguide 11 has a numerical aperture (NA) of about 0.1. It is therefore preferable to set the focal length of the external cylindrical surface lens 25 to about 2 mm. A radius R of curvature of the external cylindrical surface lens 25 is about 1 mm because $R=f/(n-1)$ where f is the focal length and n is the refractive index. The external cylindrical surface lens 25 may be formed by a plurality of lenses. However, it is preferable to form the external cylindrical surface lens by a single lens through curved surface design with aberration correction. A single lens simplifies the structure and reduces the surface reflection area.

The structures of the optical waveguide substrate 30, internal cylindrical surface lens 32, external cylindrical surface lens 35 and connector 38 respectively on the reception side are similar to those of the optical waveguide substrate 10, internal cylindrical surface lens 12, external cylindrical surface lens 25 and connector 28 respectively on the transmission side. The transmission side connector 28 and reception side connector 38 are inserted into the sleeve 40 so that the transmission side external cylindrical surface lens 25 and reception side external cylindrical surface lens 35 face each other, and that on the outer sides thereof, the transmission side internal cylindrical surface lens 12 and reception side internal cylindrical surface lens 32 face each other.

The reception side external cylindrical surface lens 35 converges the light beam 18 changed to the parallel light flux by the transmission side external cylindrical surface lens 25, along the direction in the ZX plane, and makes the light beam incident upon the internal cylindrical surface lens 32. The internal cylindrical surface lens 32 converges the light beam along the direction in the XY plane and makes the light beam incident upon the input end of the optical waveguide 31.

According to the first embodiment, the optical waveguide 11 and internal cylindrical surface lens 12 on the transmission side are formed at the same time on the same substrate. Therefore, the position alignment of both the optical waveguide and internal cylindrical surface lens can be set correctly and the position displacement to be caused by a temperature change can be avoided.

Further, since the generating line of the curved surface of the external cylindrical surface lens 25 is parallel to the Y-axis, it is not necessary to strictly perform the position alignment between the internal cylindrical surface lens 12 and external cylindrical surface lens 25 in the Y-axis direction. Even if the external cylindrical surface lens 25 is expanded or contracted by a temperature change, the position displacement will not occur.

Next, with reference to FIG. 3, an example of the structure of a positioning member for positioning the substrate 10 and external cylindrical surface lens 25 shown in FIGS. 1A and 1B and FIG. 2 will be described.

Figure 3:
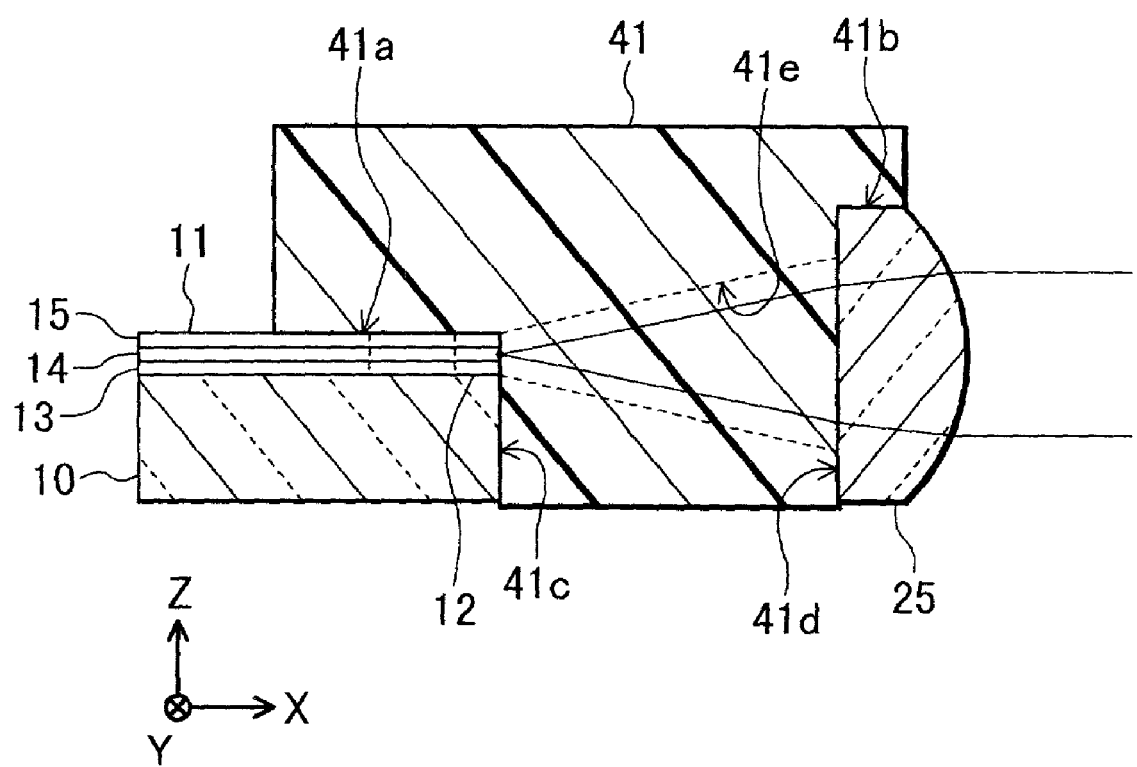
FIG. 3 is a cross sectional view of a positioning member for positioning optical waveguides and an external cylindrical surface lens.

FIG. 3 is a cross sectional view of the substrate 10, external cylindrical surface lens 25 and positioning member 41. The positioning member 41 defines a first reference plane 41a in contact with the upper surface of the upper clad 15; a second reference plane 41b in contact with the side plane of the external cylindrical surface lens 25; a third reference plane 41c in contact with the edge of the substrate 10; and a fourth reference plane 41d in contact with the plane of the external cylindrical surface lens 25 on the side of the internal cylindrical surface lens 12. A through hole 41e is formed through the positioning member in an area between the internal cylindrical surface lens 12 and external cylindrical surface lens 25 to form an optical path of a light beam.

Since the upper surface of the upper clad 15 contacts the first reference plane 41a and the side plane of the external cylindrical surface lens 25 contacts the second reference plane 41b, the relative positions of the upper clad 15 and external cylindrical surface lens 25 in the Z-axis direction can be determined correctly. Although it is difficult to set a precision of the thickness of the substrate 10 in the sub-micron order or finer, it is relatively easy to set a precision of the thickness of the upper clad 15 in the sub-micron order or finer. By using the upper surface of the upper clad 15 as the positioning reference, a positioning precision of the core 14 and external cylindrical surface lens 25 in the Z-axis direction can be improved.

Since the edge of the substrate 10 contacts the third reference plane 41c and the external cylindrical surface lens 25 contacts the fourth reference plane 41d, the internal cylindrical surface lens 12 and external cylindrical surface lens 25 can be aligned in position in the X-axis direction.

Next, with reference to FIG. 4, an optical transmission device according to the second embodiment of the invention will be described.

Figure 4:
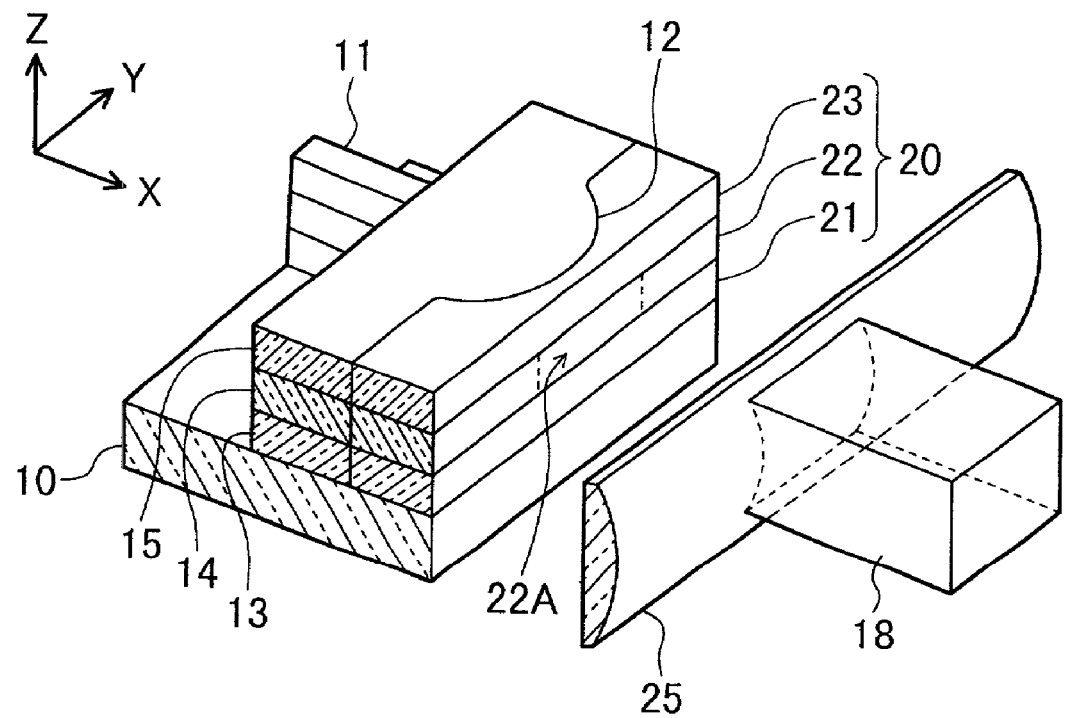
FIG. 4 is a perspective view showing the main part of an optical transmission device according to a second embodiment.

FIG. 4 is a perspective view partially broken of the main part of the optical transmission device of the second embodiment. Similar to the first embodiment shown in FIG. 2, an optical waveguide 11 and an internal cylindrical surface lens 12 are formed on a substrate 10, each having a lamination of a lower clad 13, a core 14 and an upper clad 15. In the first embodiment, the plane of the internal cylindrical surface lens 12 on the output side is exposed. In the second embodiment, the plane of the internal cylindrical surface lens 12 is covered with an optical waveguide layer 20.

The optical waveguide layer 20 has a three-layer structure of a lower clad 21, a core 22 and an upper clad 23 stacked in this order from the substrate 10 side. The lower clad 21, core 22 and upper clad 23 are in contact with the lower clad 13, core 14 and upper clad 15 of the internal cylindrical surface lens 12. The refractive index of the core 22 partially constituting the optical waveguide layer 20 is smaller than that of the core 14 of the internal cylindrical surface lens 12. The refractive indices of the upper and lower clads 23 and 21 of the optical waveguide layer 20 are smaller than those of the upper and lower clads 15 and 13 of the internal cylindrical surface lens 12. The end plane 22A of the optical waveguide layer 20 on the external cylindrical surface lens 25 is perpendicular to the X-axis.

In the first embodiment shown in FIG. 2, the light beam transmitted through the internal cylindrical surface lens 12 diverges along the directions in the ZX plane. The curved surface of the internal cylindrical surface lens 12 is a convex curve directing toward the external cylindrical surface lens 25. Therefore, the X-coordinate values of radiation points of the light beam diverging along the directions in the ZX plane are not the same but different. This different X-coordinate values result in aberration at the time of collimation by the external cylindrical surface lens 25.

In the second embodiment shown in FIG. 4, the light beam transmitted through the internal cylindrical surface lens 12 becomes incident upon the optical waveguide layer 20. Since the light beam is confined in the core 22 of the optical waveguide layer 20, the light beam will not diverge along the directions in the ZX plane in the optical waveguide layer 20, and starts diverging at the end plane 22A on the output side. Since the end plane 22A on the output side is perpendicular to the X-axis, aberration at the time of collimation by the external cylindrical surface lens 25 can be reduced.

Next, the internal cylindrical surface lens 12 and optical waveguide layer 20 of the optical transmission device of the second embodiment will be described. Photopolymer is coated on the surface of the substrate and patterned to form the lower clad 13 of the optical waveguide 11 and internal cylindrical surface lens 12. Photopolymer is further coated on the substrate and patterned to form the lower clad 21 of the optical waveguide layer 20. Since a swell is generally formed near at the junction between the lower clads 13 and 21, the surface is planarized by chemical mechanical polishing (CMP). By repeating similar processes, the cores 14 and 22 and upper clads 15 and 23 can be formed.

In the second embodiment shown in FIG. 4, although the optical waveguide layer 20 is a slab optical waveguide of the three-layer structure, the optical waveguide layer may be made of a single layer. If the optical waveguide layer 20 is made of a single layer, a light beam cannot be confined in the core. However, divergence along the directions in the ZX plane can be suppressed more than if the light beam is radiated directly in the air from the internal cylindrical surface lens 12.

In the second embodiment, although the end plane of the optical waveguide layer 20 on the output side is flat, it is not necessarily required that the end plane on the output side is flat. The configuration of the end plane of the optical waveguide layer 20 on the output side may be designed so that a difference between the longest and shortest lengths of optical paths of a light beam radiating from the end plane of the optical waveguide layer 20 on the output side and reaching the external cylindrical surface lens 25 becomes smaller than a difference between the longest and shortest lengths of optical paths of a light beam radiating from the internal cylindrical surface lens 12 and reaching the external cylindrical surface lens 25. Also in this case, the reduction effects of aberration at the time of collimation by the external cylindrical surface lens 25 can be expected.

Next, with reference to FIGS. 5A and 5B, an optical transmission device according to the third embodiment of the invention will be described.

Figure 5A:
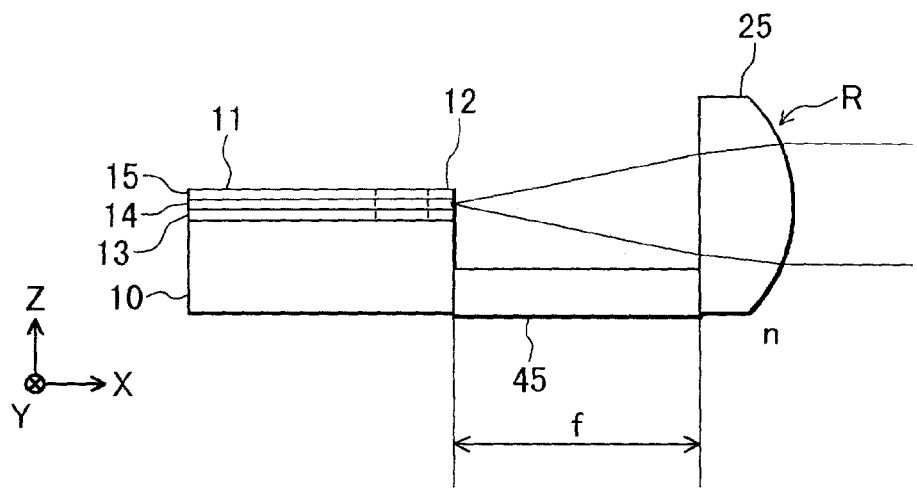
FIGS. 5A and 5B are schematic diagrams showing the main part of an optical transmission device according to a third embodiment.

As shown in FIG. 5A, an optical waveguide 11 and an internal cylindrical surface lens 12 are formed on the surface of a substrate 10, and an external cylindrical surface lens 25 is disposed on the optical path of a light beam transmitted through the internal cylindrical surface lens 12. This configuration is similar to the first embodiment shown in FIGS. 1A and 1B and FIG. 2. A distance regulating member 45 is disposed between the substrate 10 and external cylindrical surface lens 25. The distance between the substrate 10 and external cylindrical surface lens 25 is changed when the distance controlling member 45 is thermally expanded. The distance is regulated in such a manner that the plane of the internal cylindrical surface lens 12 on the output side becomes coincident with the focal point of the external cylindrical surface lens 25.

Figure 5B:
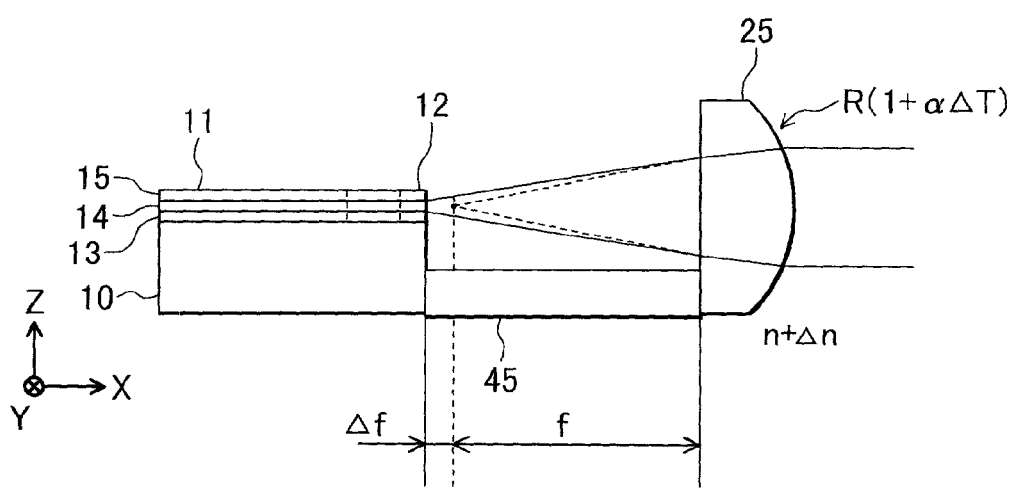

As shown in FIG. 5B, as the temperature rises, the focal length f of the external cylindrical surface lens 25 is elongated and the distance regulating member 45 is also elongated to increase the distance between the substrate 10 and external cylindrical surface lens 25. By representing an elongated length of the focal length f by $\Delta f$ and representing an increased distance between the internal cylindrical surface lens 12 and external cylindrical surface lens 25 by $\Delta g$, if $\Delta f - \Delta g$ is 0, it is possible to almost perfectly compensate a change in the focal length of the external cylindrical surface lens 25. If the absolute value of $\Delta f - \Delta g$ is smaller than $\Delta f$, the compensation effects of a focal length change can be expected.

Consider now that the curved surface of the external cylindrical surface lens 25 has a circular cylindrical surface. The elongated length $\Delta f$ of the focal length when a temperature is raised by $\Delta T$ is given by:

$$\Delta f = R(1+\alpha \Delta T)/(n+\Delta n \Delta T-1) - R/(n-1)$$

where n is a refractive index of the external cylindrical surface lens 25 at the room temperature, R is the radius of curvature of the circular cylindrical surface, $\Delta n$ is a refractive index change rate per 1° C., and $\alpha$ is a coefficient of linear expansion. If the external cylindrical surface lens 25 is made of quartz, n=1.445, $\Delta n = 1 \times 10^{-5}$/° C. and $\alpha = 0.4 \times 10^{-6}$/°C. If the radius R of curvature is 2 mm and the temperature rise width $\Delta T$ is 100° C., then $\Delta f$ is 0.010 mm.

Under these conditions, the focal length f at the room temperature is about 4.5 mm. If the material of the distance regulating member 45 has a coefficient of linear expansion of $2.2 \times 10^{-5}/°$ C., a change in the focal length at the temperature rise of 100° C. can be almost perfectly compensated. Such material is, for example, aluminum.

Figure 6:
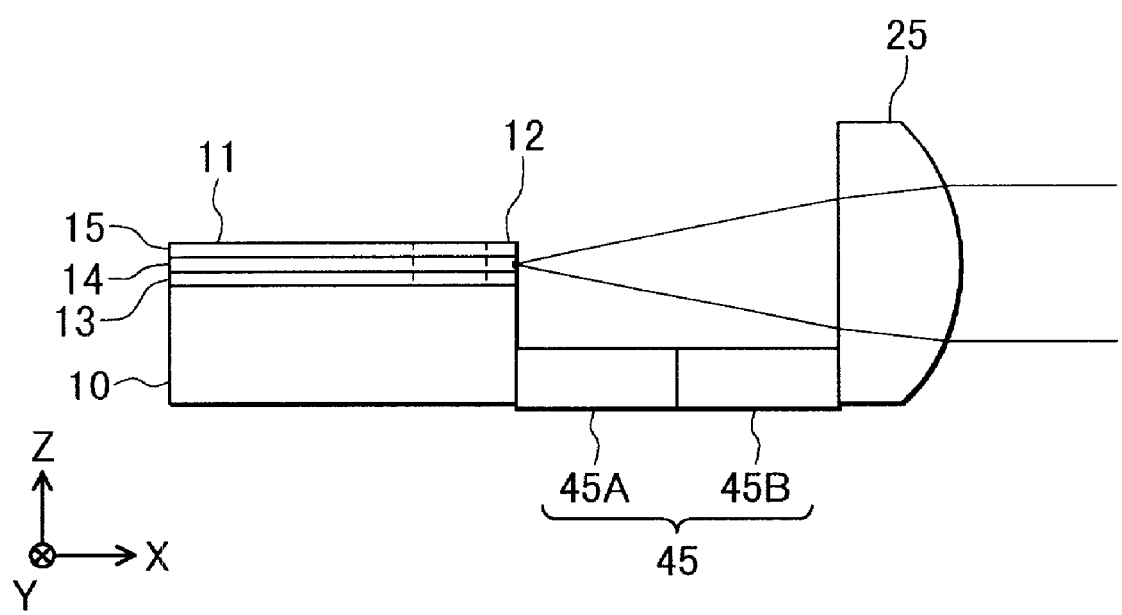
FIG. 6 is a schematic diagram showing the main part of an optical transmission device according to a modification of the third embodiment.

FIG. 6 is a schematic diagram of an optical transmission device according to a modification of the third embodiment. In the third embodiment shown in FIGS. 5A and 5B, the distance regulating member is a single discrete member. In this modification, a distance regulating member 45 is made of two members 45A and 45B juxtaposed along the X-axis direction. The two members 45A and 45B are made of materials having different coefficients of linear expansion.

Under the conditions described with the third embodiment, it is possible to find the material having a desired coefficient of linear expansion. There is a case that proper material having a desired coefficient of linear expansion cannot be found. In such a case, as shown in FIG. 6, by using two members 45A and 45B of the distance regulating member 45, an effective coefficient of linear expansion can be set near at the desired coefficient. The effective coefficient of linear expansion of the distance regulating member 45 can be given by:

$$L_A \alpha_A/(L_A+L_B) + L_B \alpha_B/(L_A+L_B)$$

where $L_A$ is a length of the member 45A in the X-axis direction, $\alpha_A$ is a coefficient of linear expansion, $L_B$ is a length of the member 45B in the X-axis direction, $\alpha_B$ is a coefficient of linear expansion.

Next, with reference to FIG. 7, an optical transmission device according to the fourth embodiment of the invention will be described.

Figure 7:
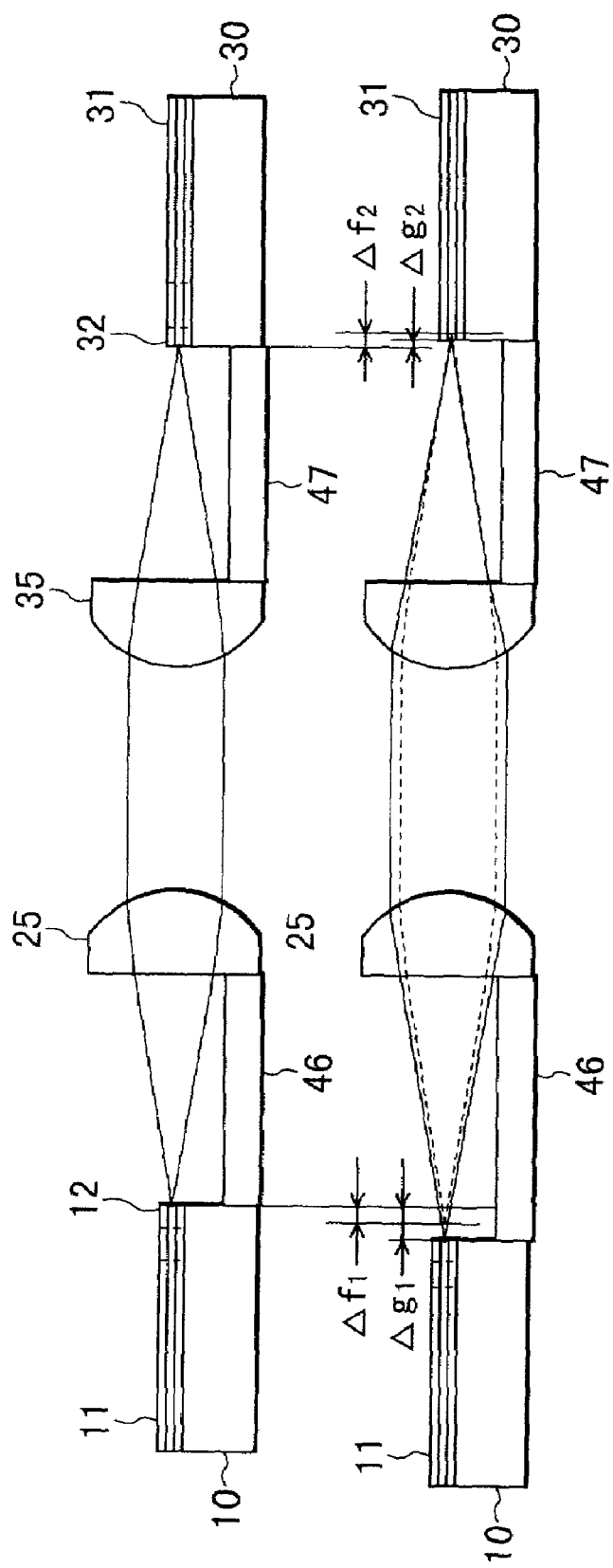
FIG. 7 is a schematic diagram showing the main part of an optical transmission device according to a fourth embodiment.

FIG. 7 is a schematic diagram showing the optical transmission device of the fourth embodiment. The structures of an optical waveguide substrate 10 and an external cylindrical surface lens 25 respectively on the transmission side and the structures of an optical waveguide substrate 30 and an external cylindrical surface lens 35 respectively on the reception side are similar to those of the optical transmission device of the first embodiment shown in FIGS. 1A and 1B and FIG. 2. On the transmission side, the distance between the substrate 10 and external cylindrical surface lens 25 is regulated by a distance regulating member 46, and on the reception side, the distance between the substrate 30 and external cylindrical surface lens 35 is regulated by another distance regulating member 47.

Elongated lengths of the focal lengths of the external cylindrical surface lenses 25 and 35 when a temperature rises are represented by $\Delta f_1$ and $\Delta f_2$, and increased distances of the distance regulating members 46 and 47 caused by thermal expansion are represented by $\Delta g_1$ and $\Delta g_2$. The materials of the distance regulating members 46 and 47 are selected so that the absolute value of $\Delta f_1 - \Delta g_1 + \Delta f_2 - \Delta g_2$ becomes smaller than the absolute value of $\Delta f_1 + \Delta f_2$. It is therefore possible to mitigate the influence of a shift of the focal points to be caused by a change in the focal lengths of the external cylindrical surface lenses 25 and 35.

In the example shown in FIG. 7, $\Delta g_1 > \Delta f_1$ and $\Delta g_2 < \Delta f_2$. In the third embodiment, the ideal case $\Delta g_1 = \Delta f_1$ on the transmission side and $\Delta g_2 = \Delta f_2$ on the reception side. In the fourth embodiment, the influence of a temperature change is mitigated as the total of the transmission and reception sides. In this embodiment, the light beam between the external cylindrical surface lenses 25 and 35 is not a parallel light flux in the strict sense. However, the influence of not a parallel light flux is expected to be small.

If the connector of the optical transmission device satisfying the condition of $\Delta g_1 > \Delta f_1$ is a male connector and the connector of the optical transmission device satisfying the condition of $\Delta g_2 < \Delta f_2$ is a female connector, these connectors can be mounted on the optical transmission device without checking the coefficients of linear expansion of the distance regulating members.

Figure 8A:
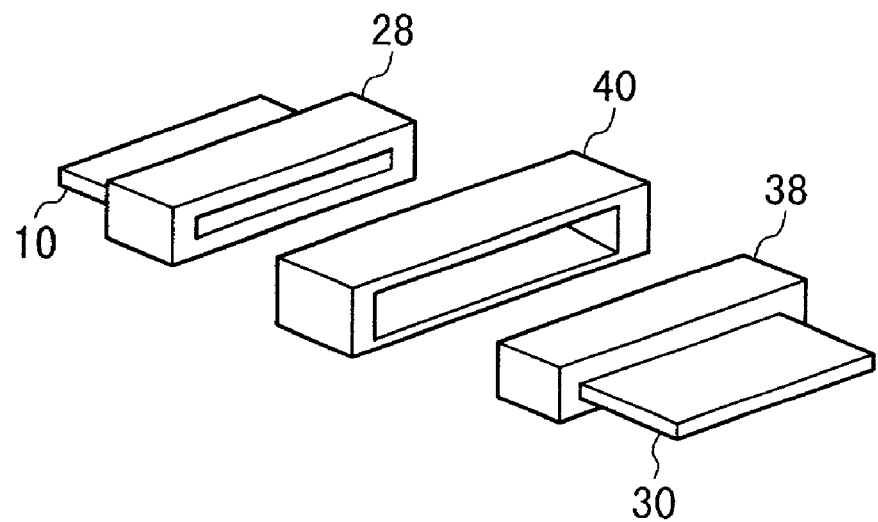
FIGS. 8A and 8B are perspective views of connectors and sleeves.
Figure 9A:
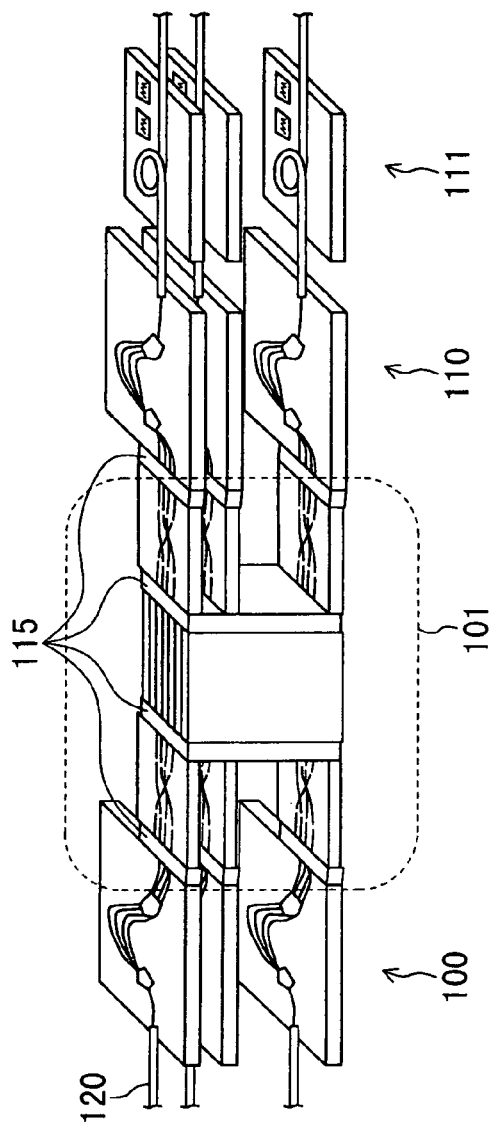
FIG. 9A is a schematic diagram showing an optical switch.
Figure 9B:
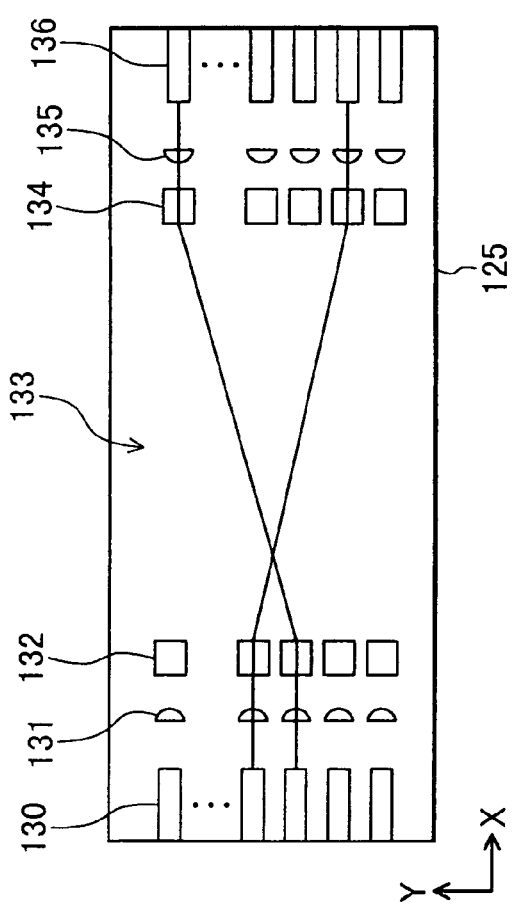
FIG. 9B is a plan view of an optical switch substrate.

FIG. 8A is a perspective view of a transmission side connector 28, a reception side connector 38 and a sleeve 40 for coupling both the connectors together. An optical waveguide substrate 10 with the transmission side connector 28 and an optical waveguide substrate 30 with the transmission side connector 38 are disposed along the same plane. This connection configuration is utilized for the connection between the optical splitter 100 shown in FIG. 9A and the first stage of the optical switch module 101 and for the connection between the third stage of the optical switch module 101 and the optical multiplexer 110.

Figure 8B:
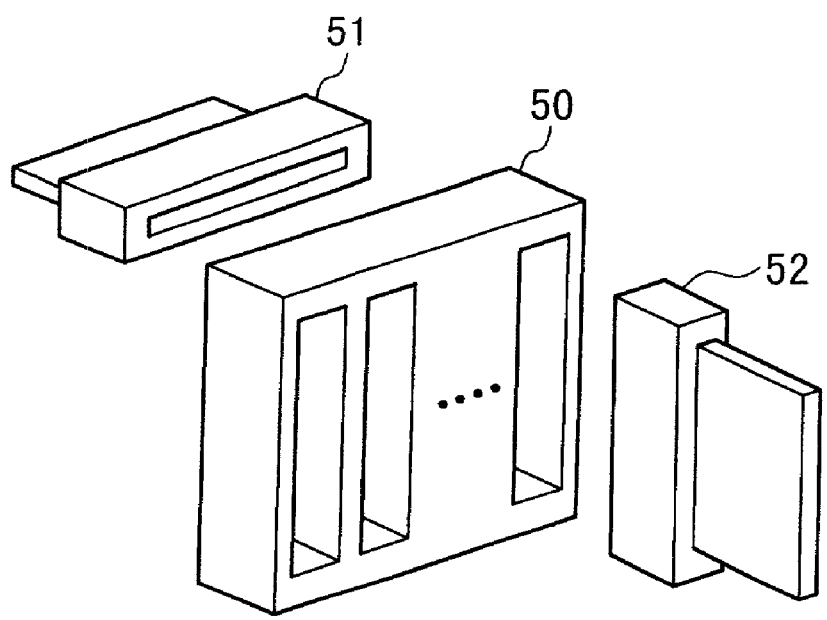

FIG. 8B shows another structure of a sleeve. Slots formed on one side of the sleeve 50 are perpendicular to slots formed on the opposite side. A transmission side connector 51 is inserted into a slot on one side, and a reception side connector 52 is inserted into a slot on the opposite side. As viewed in parallel to the propagation direction of a light beam, the direction of output ends of transmission side optical waveguides are perpendicular to the direction of input ends of reception side optical waveguides. This connection configuration is utilized for the connection between the first and second stages of the optical switch module 101 shown in FIG. 9A and for the connection between the second and third stages.

The optical transmission devices of the first to fourth embodiments are applicable to both the connection configurations shown in FIGS. 8A and 8B.

The present invention has been described in connection with the preferred embodiments. The invention is not limited only to the above embodiments. It is apparent that various modifications, improvements, combinations, and the like can be made by those skilled in the art.

What we claim are:

1. An apparatus comprising:

an optical waveguide end structure formed on an underlying surface, said optical waveguide end structure including an optical waveguide guiding light along a first direction parallel to the underlying surface and first converging means formed on the underlying surface and being continuous with the optical waveguide at an end of the optical waveguide, said optical waveguide and said first converging means having a same laminated structure, said first converging means for converging light radiated from the end of said optical waveguide and diverging along directions parallel to the underlying surface, and light being propagated in said first converging means is confined in a direction perpendicular to the underlying surface;

second converging means for converging light transmitted through said first converging means and diverging along directions perpendicular to the underlying; and a support member for supporting said first converging means and said second converging means, said support member comprising a distance regulating member for regulating a distance between said first converging means and said second converging means, said distance regulating member changes the distance between said first converging means and said second converging means through thermal expansion, and a coefficient of linear expansion of said distance regulating member is selected in such a manner that an absolute value of Δf−Δg becomes smaller than Δf where Δf is an elongated length of a focal length of said second converging means and Δg is an increased distance between said first converging means and said second converging means, respectively when a temperature changes from a first temperature to a second temperature.

2. An optical transmission device comprising:
at least one optical waveguide end structure formed on an underlying surface, said optical waveguide end structure including an optical waveguide for guiding light along a first direction parallel to the underlying surface and a first lens formed on the underlying surface and being continuous with the optical waveguide at one end thereof, said first lens converging light that is radiated from the end of said optical waveguide and diverges along directions parallel to the underlying surface;
a second lens for converging light that is transmitted through said first lens and diverges along directions perpendicular to the underlying surface; and
a support member for supporting said first and second lenses,
wherein said support member comprises a distance regulating member for regulating a distance between said first and second lenses, said distance regulating member changes the distance between said first and second lenses through thermal expansion, and a coefficient of linear expansion of said distance regulating member is selected in such a manner that an absolute value of Δf−Δg becomes smaller than Δf where Δf is an elongated length of a focal length of said second lens and Δg is an increased distance between said first and second lenses, respectively when a temperature changes from a first temperature to a second temperature.

3. An optical transmission device according to claim 2, wherein:
a shape of a surface of said first lens facing said second lens is convex toward said second lens as viewed along a direction perpendicular to the underlying surface; and
said optical waveguide end structure further comprises an optical waveguide layer in tight contact with said first lens on the surface facing said second lens, said optical waveguide layer guiding light radiated from said first lens and having an end surface facing said second lens, the end surface having a shape so that a difference between longest and shortest lengths of optical paths of light radiated from the end surface and reaching said second lens is smaller than that between longest and shortest lengths of optical paths of light radiated from said first lens and reaching said second lens.

4. An optical transmission device according to claim 3, wherein
said optical waveguide and said first lens each have a three-layer structure having a lower clad, a core and an upper clad stacked in this order, and
said optical waveguide layer has a three-layer structure having a lower clad, a core and an upper clad stacked in this order, and a refractive index of the core of said optical waveguide layer is smaller than that of the core of said optical waveguide.

5. An optical transmission device according to claim 2, wherein said optical waveguide and said first lens each have a three-layer structure having a lower clad, a core and an upper clad stacked in this order.

6. An optical transmission device according to claim 2, wherein a plurality of said optical waveguide end structures are disposed along a second direction crossing the first direction, and said second lens is a cylindrical surface lens having a cylindrical surface parallel to the second direction and optically coupled to said optical waveguide end structures.

7. An optical transmission device according to claim 6, wherein said first lens of each of said optical waveguide end structures has a same shape, and a first lens of a respective optical waveguide end structure is superposed upon a first lens of a different optical waveguide end structure by moving the first lens of said respective optical waveguide end structure in parallel to the second direction.

8. An optical transmission device according to claim 2, wherein said distance regulating member comprises at least two members disposed along a propagation direction of light between said first and second lenses, and said two members have different coefficients of linear expansion.

9. An optical transmission device according to claim 2, wherein said support member has a first reference plane in contact with an upper surface of said optical waveguide end structure and a second reference plane in contact with said second lens for regulating a position of said second lens along a direction perpendicular to the underlying surface, and said support member fixes a relative position of said optical waveguide end structure and said second lens along the direction perpendicular to the underlying surface.

10. An optical transmission device according to claim 2, wherein said support member has a reference plane in contact with said optical waveguide end structure on an end surface facing said second lens and a reference plane in contact with said second lens for regulating a position of said second lens along the first direction.

11. An optical transmission device according to claim 2, wherein the first lens converges light emitted from the end of the optical waveguide in a plane parallel to the underlying surface, and the second lens converges light passing through the first lens in a plane perpendicular to the underlying surface.

12. An optical transmission device according to claim 2, wherein the light emitted from the end of the optical waveguide diverges in a direction parallel to the underlying surface but does not diverge in a direction perpendicular to the underlying surface between the end of the optical waveguide and the first lens.

13. An optical transmission device according to claim 2, wherein the first lens serves as an optical waveguide in a direction perpendicular to the underlying surface, so that the first lens thereby confines the light being propagated in the first lens in the direction perpendicular to the underlying surface.

14. An optical transmission device comprising:
first and second optical connectors each having an optical waveguide end structure, a second lens and a support member, the optical waveguide end structure being formed on an underlying surface and including an optical waveguide for guiding light along a first direction parallel to the underlying surface and a first lens being formed on the underlying surface and being continuous with the optical waveguide at one end thereof, the first lens converging light that is radiated from the end of the optical waveguide and diverges along directions parallel to the underlying surface, the second lens converging light that is transmitted through the first lens and diverges along directions perpendicular to the underlying surface, and the support member supporting the first and second lenses; and a coupling member for removably coupling said first and second optical connectors so that a light beam propagating in the optical waveguide of said first optical connector and converged by the first and second lenses is converged by the second and first lenses of said second optical connector toward one end of the optical waveguide of said second optical connector, wherein each support member of said first and second optical connectors comprises a distance regulating member for regulating a distance between the first and second lenses, the distance regulating member changes the distance between the first and second lenses through thermal expansion, and a coefficient of linear expansion of the distance regulating member is selected in such a manner that an absolute value of $\Delta f_1 - \Delta g_1 + \Delta f_2 - \Delta g_2$ becomes smaller than an absolute value of $\Delta f_1 + \Delta f_2$ where $\Delta f1$ is an elongated length of a focal length of the second lens of said first optical connector, $\Delta g_1$ is an increased distance between the first and second lenses of said first optical connector, $\Delta f_2$ is an elongated length of a focal length of the second lens of said second optical connector, and $\Delta g_2$ is an increased distance between the first and second lenses of said second optical connector, respectively when a temperature changes from a first temperature to a second temperature.

15. An optical transmission device according to claim 14, wherein the first lens serves as an optical waveguide in a direction perpendicular to the underlying surface, so that the first lens thereby confines the light being propagated in the first lens in the direction perpendicular to the underlying surface.

* * * * *

UNITED STATES PATENT AND TRADEMARK OFFICE
CERTIFICATE OF CORRECTION

PATENT NO. : 7,099,534 B2
APPLICATION NO. : 10/158016
DATED : August 29, 2006
INVENTOR(S) : Masayuki Kato et al.

It is certified that error appears in the above-identified patent and that said Letters Patent is hereby corrected as shown below:

Column 10, Line 58, change "underlying;" to --underlying surface;--.

Column 13, Line 17, change "$\Delta f1$" to --$\Delta f_1$--.

Signed and Sealed this

Twentieth Day of February, 2007

JON W. DUDAS
*Director of the United States Patent and Trademark Office*